US012390183B2

(12) United States Patent
Inoue et al.

(10) Patent No.: US 12,390,183 B2
(45) Date of Patent: Aug. 19, 2025

(54) ENDOSCOPE SYSTEM AND ENDOSCOPE IMAGE DISPLAY CONTROL METHOD

(71) Applicants: Haruhiro Inoue, Tokyo (JP); OLYMPUS CORPORATION, Tokyo (JP)

(72) Inventors: Haruhiro Inoue, Tokyo (JP); Takefumi Uesugi, Tachikawa (JP)

(73) Assignee: OLYMPUS CORPORATION, Tokyo (JP)

( * ) Notice: Subject to any disclaimer, the term of this patent is extended or adjusted under 35 U.S.C. 154(b) by 564 days.

(21) Appl. No.: 17/888,811

(22) Filed: Aug. 16, 2022

(65) Prior Publication Data
US 2023/0089053 A1 Mar. 23, 2023

Related U.S. Application Data

(63) Continuation of application No. PCT/JP2020/006561, filed on Feb. 19, 2020.

(51) Int. Cl.
*A61B 5/00* (2006.01)
*A61B 1/00* (2006.01)
(Continued)

(52) U.S. Cl.
CPC .......... *A61B 7/023* (2013.01); *A61B 1/00009* (2013.01); *A61B 1/0005* (2013.01);
(Continued)

(58) Field of Classification Search
CPC ... A61B 7/023; A61B 1/00009; A61B 1/0005; A61B 1/00055; A61B 5/037;
(Continued)

(56) References Cited

U.S. PATENT DOCUMENTS

| 5,878,749 A * | 3/1999 | Miller .................... A61B 5/037 |
| | | 600/455 |
| 2004/0138586 A1 | 7/2004 | Ganz et al. |

(Continued)

FOREIGN PATENT DOCUMENTS

| EP | 2 850 998 A1 | 3/2015 |
| JP | H05-245100 A | 9/1993 |

(Continued)

OTHER PUBLICATIONS

International Search Report dated Apr. 14, 2020 received in PCT/JP2020/006561.

(Continued)

*Primary Examiner* — May A Abouelela
(74) *Attorney, Agent, or Firm* — Scully, Scott, Murphy & Presser, P.C.

(57) ABSTRACT

An endoscopic system includes a processor. The processor generates from a measured value of pressure in a lumen of a subject a first temporal change image of the pressure in the lumen, generates an observation image for observing an opened/closed state of a valve portion in the lumen of the subject in real time from an image pickup signal obtained by picking up an image of the opened/closed state of the valve portion in the lumen in real time using an endoscope, and generates a superposition image by superposing the first temporal change image and the observation image in a temporally synchronized manner.

18 Claims, 11 Drawing Sheets

(51) Int. Cl.
  *A61B 5/03* (2006.01)
  *A61B 7/00* (2006.01)
  *A61B 7/02* (2006.01)
  *A61M 13/00* (2006.01)
  *G06T 7/00* (2017.01)
  *G06T 7/20* (2017.01)
  *G06T 11/00* (2006.01)
  *A61B 1/273* (2006.01)

(52) U.S. Cl.
  CPC .......... *A61B 1/00055* (2013.01); *A61B 5/037* (2013.01); *A61B 7/008* (2013.01); *A61M 13/003* (2013.01); *G06T 7/0016* (2013.01); *G06T 7/20* (2013.01); *G06T 11/00* (2013.01); *A61B 1/2733* (2013.01); *G06T 2207/10068* (2013.01); *G06T 2207/30092* (2013.01); *G06T 2210/41* (2013.01)

(58) Field of Classification Search
  CPC ... A61B 7/008; A61B 1/2733; A61B 1/00006; A61B 1/000095; A61B 1/00097; A61B 5/4233; A61B 5/4255; A61B 5/7425; A61B 5/743; A61B 2505/05; A61B 2562/0204; A61B 2562/0247; A61B 2576/02; A61B 1/015; A61B 1/045; A61B 10/00; A61M 13/003; A61M 16/0461; G06T 7/0016; G06T 7/20; G06T 11/00; G06T 2207/10068; G06T 2207/30092; G06T 2210/41; G06T 7/0012
  See application file for complete search history.

(56) References Cited

U.S. PATENT DOCUMENTS

| | | | |
|---|---|---|---|
| 2005/0222535 A1* | 10/2005 | Uesugi | A61B 1/3132 600/560 |
| 2005/0228294 A1 | 10/2005 | Yamaki | |
| 2006/0058617 A1* | 3/2006 | Sano | A61B 1/3132 600/407 |
| 2006/0116586 A1* | 6/2006 | Sekiguchi | A61B 1/12 600/470 |
| 2007/0244363 A1* | 10/2007 | Sano | A61M 13/003 600/118 |
| 2007/0292011 A1* | 12/2007 | Nishimura | A61B 5/7264 382/128 |
| 2010/0094137 A1* | 4/2010 | Furlong | A61B 1/32 600/476 |
| 2011/0273548 A1* | 11/2011 | Uchiyama | A61B 1/00158 348/E7.085 |
| 2012/0053413 A1* | 3/2012 | Yoshida | A61B 1/0638 600/118 |
| 2012/0101334 A1* | 4/2012 | Banik | A61B 1/31 604/23 |
| 2012/0253124 A1* | 10/2012 | Torisawa | A61B 1/126 600/118 |
| 2012/0277532 A1* | 11/2012 | Torisawa | A61B 1/015 600/118 |
| 2013/0012815 A1* | 1/2013 | Kubo | A61B 5/073 600/431 |
| 2013/0323673 A1 | 12/2013 | Hakomori et al. | |
| 2014/0155709 A1* | 6/2014 | Ikai | A61B 1/00158 600/302 |
| 2015/0080757 A1* | 3/2015 | Torisawa | A61B 1/31 600/560 |
| 2016/0029998 A1* | 2/2016 | Brister | A61B 8/0833 600/424 |
| 2017/0238839 A1* | 8/2017 | Hyde | A61B 5/062 |
| 2017/0238840 A1* | 8/2017 | Hyde | A61B 5/6882 |
| 2017/0290542 A1* | 10/2017 | Chandrasoma | A61B 5/4233 |
| 2018/0132703 A1* | 5/2018 | Reever | A61B 1/05 |
| 2018/0184892 A1* | 7/2018 | Truckai | A61B 1/303 |
| 2018/0214197 A1* | 8/2018 | Hiraga | A61B 18/1402 |
| 2019/0065970 A1* | 2/2019 | Bonutti | G16H 20/10 |
| 2019/0134279 A1* | 5/2019 | Benamou | A61B 18/148 |
| 2019/0307316 A1* | 10/2019 | Levy | A61B 1/015 |
| 2020/0008687 A1* | 1/2020 | Friedlander | A61B 3/16 |
| 2020/0175719 A1* | 6/2020 | Wright | G06T 7/74 |
| 2020/0297403 A1* | 9/2020 | Kochavi | A61B 90/06 |
| 2021/0007810 A1* | 1/2021 | Rainis | A61B 34/20 |
| 2021/0059759 A1* | 3/2021 | Asirvatham | A61B 18/00 |
| 2021/0251654 A1* | 8/2021 | Pegman | A61B 17/3421 |
| 2021/0402108 A1* | 12/2021 | Spence | A61B 1/127 |

FOREIGN PATENT DOCUMENTS

| | | |
|---|---|---|
| JP | H11-347043 A | 12/1999 |
| JP | 2003-010105 A | 1/2003 |
| JP | 2005-095567 A | 4/2005 |
| JP | 2006-020788 A | 1/2006 |
| JP | 2006-061214 A | 3/2006 |
| JP | 2014-004329 A | 1/2014 |
| JP | 2015-058120 A | 3/2015 |
| JP | 2016-214516 A | 12/2016 |
| JP | 3209885 U | 4/2017 |

OTHER PUBLICATIONS

Suzuki, T. et al., "Examination of Visceral Perception and Gastric Tone by Gastric Stimulation Using Air Inflation during Endoscopy", The Journal of International Medical Research, Mar. 1, 2005, vol. 33, No. 2, pp. 160-169.

Kira, F. et al., "Response to Air Insufflation in Patients with Non-erosive Gastro-oesophageal Reflux Disease (NERD)", The Journal of International Medical Research, Feb. 1, 2011, vol. 39, No. 1, pp. 215-221.

Noue, H., et al., "Diagnostic performance of the endoscopic pressure study integrated system (EPSIS): a novel diagnostic tool for gastroesophageal reflux disease", Performance of the EPSIS system for diagnosis of GERD . . . Endoscopy, 2019; 51; pp. 759-762.

* cited by examiner

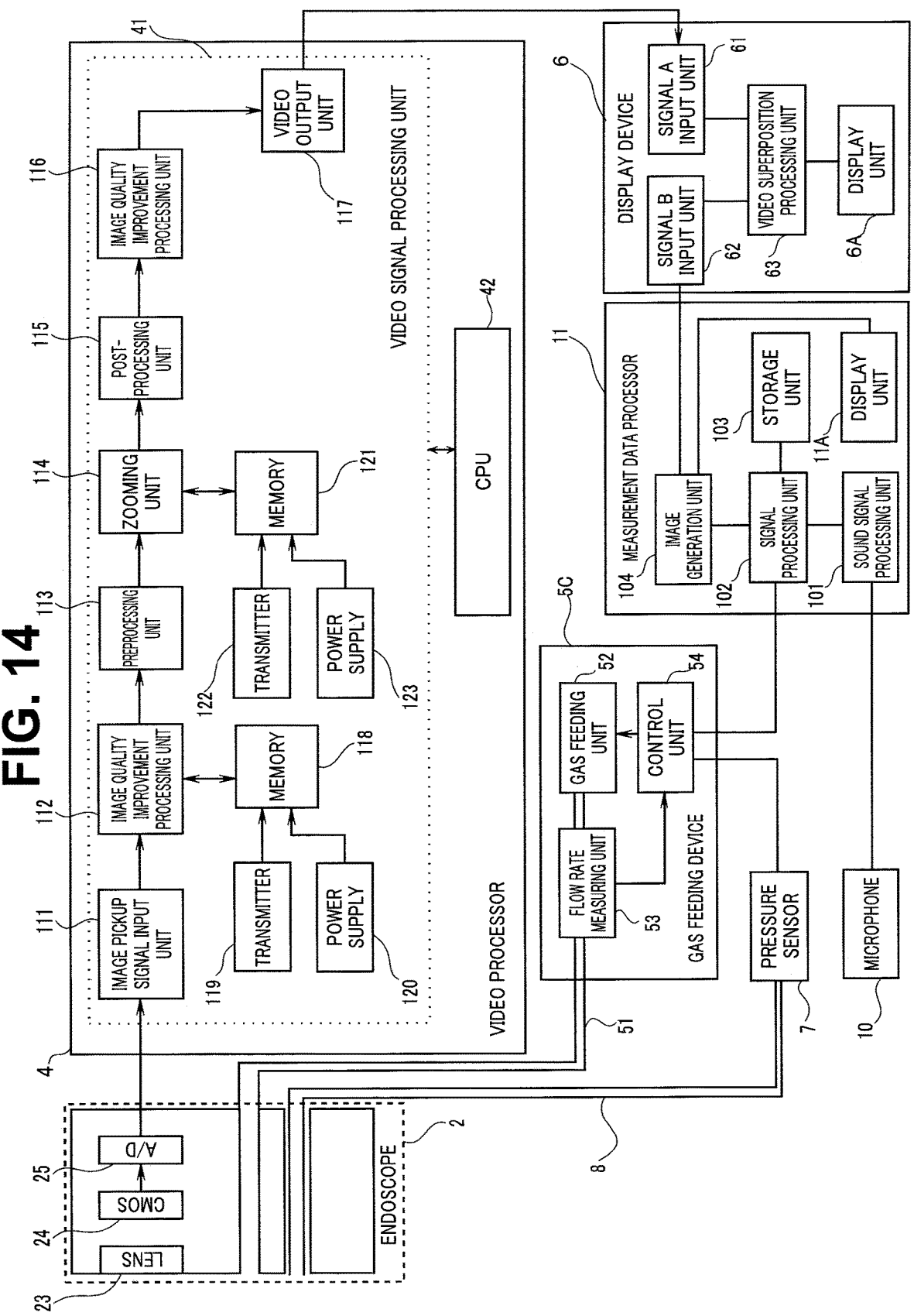

ENDOSCOPE SYSTEM AND ENDOSCOPE IMAGE DISPLAY CONTROL METHOD

CROSS REFERENCE TO RELATED APPLICATION

This application is a continuation application of PCT/JP2020/006561 filed on Feb. 19, 2020, the entire contents of which are incorporated herein by this reference.

BACKGROUND OF THE INVENTION

1. Field of the Invention

Embodiments of the present invention relate to an endoscopic system and an endoscopic image display control method, and in particular, relate to an endoscopic system and an endoscopic image display control method for use in diagnosing gastroesophageal reflux disease.

2. Description of the Related Art

Conventionally, a method called 24-hour esophagus pH monitoring or 24-hour esophagus impedance-pH monitoring is used as a diagnostic method for gastroesophageal reflux disease (hereinafter referred to as GERD) that is a disease in which the function of the cardiac part of the stomach deteriorates and gastric juice flows back up into the esophagus.

In recent years, to reduce burdens on patients, a method for observing the relaxed state of the lower esophageal sphincter (LES) of the cardiac part of the stomach using an endoscope has been applied. Meanwhile, there has been proposed an endoscopic system for evaluating the swallowing function by combining endoscopic observation and evaluation of a swallowing sound (for example, see the publication of Japanese Utility Model Registration No. 3209885). With the endoscopic system disclosed in the publication, evaluation of the swallowing function is possible.

SUMMARY OF THE INVENTION

An endoscopic system according to an aspect of the present invention includes a processor, the processor being configured to execute: generating from a measured value of pressure in a lumen of a subject a first temporal change image that is an image showing a temporal change in the pressure in the lumen, generating an observation image for observing an opened/closed state of a valve portion in the lumen of the subject in real time from an image pickup signal obtained by picking up an image of the opened/closed state of the valve portion in the lumen in real time using an endoscope, and generating a first superposition image by superposing the first temporal change image and the observation image in a temporally synchronized manner.

An endoscopic image display control method according to an aspect of the present invention includes generating from a measured value of pressure in a lumen of a subject a first temporal change image that is an image showing a temporal change in the pressure in the lumen; generating an observation image for observing an opened/closed state of a valve portion in the lumen of the subject in real time from an image pickup signal obtained by picking up an image of the opened/closed state of the valve portion in the lumen in real time using the endoscope; and generating a first superposition image by superposing the first temporal change image and the observation image in a temporally synchronized manner.

An endoscopic system according to another aspect of the present invention includes a processor, the processor being configured to execute: generating from a measured value of pressure in a lumen of a subject a first temporal change image that is an image showing a temporal change in the pressure in the lumen, generating an observation image for observing an opened/closed state of a valve portion in the lumen of the subject from an image pickup signal obtained by picking up an image of the opened/closed state of the valve portion in the lumen using an endoscope, generating a first superposition image by superposing the first temporal change image and the observation image in a temporally synchronized manner, and measuring a gas release sound released from the lumen of the subject to generate a second temporal change image that is an image showing a temporal change in the gas release sound from a measured value of the gas release sound, and generating a second superposition image by superposing the first temporal change image, the second temporal change image, and the observation image in a temporally synchronized manner.

BRIEF DESCRIPTION OF THE DRAWINGS

FIG. 14 is a block diagram illustrating an example of a functional configuration of the endoscopic system according to the fourth embodiment.

DETAILED DESCRIPTION OF THE PREFERRED EMBODIMENTS

Typically, a conventional diagnostic method (i.e., 24-hour esophagus pH monitoring or 24-hour esophagus impedancepH monitoring) for gastroesophageal reflux disease (GERD) requires insertion of a measuring tube through the nose for 24 hours. Therefore, there has been a problem that the burden on the patient is big. There has also been a problem that such a conventional diagnostic method requires a long time to obtain a result of the diagnosis.

To improve such problems, a method for observing the relaxed state of the lower esophageal sphincter (LES) of the cardiac part of the stomach using an endoscope has been applied in recent years, in particular, to reduce burdens on patients.

However, it is difficult to distinguish GERD from other diseases by performing endoscopic observation alone.

Further, the conventional endoscopic system disclosed in the publication of Japanese Utility Model Registration No. 3209885, for example, has not solved the problem that it is difficult to distinguish GERD from other diseases.

Accordingly, the present invention can provide an endoscopic system that can reduce burdens on a patient being tested for gastroesophageal reflux disease, and can promptly obtain a result of diagnosis.

Hereinafter, embodiments will be described with reference to the drawings.

First Embodiment

Figure 1:
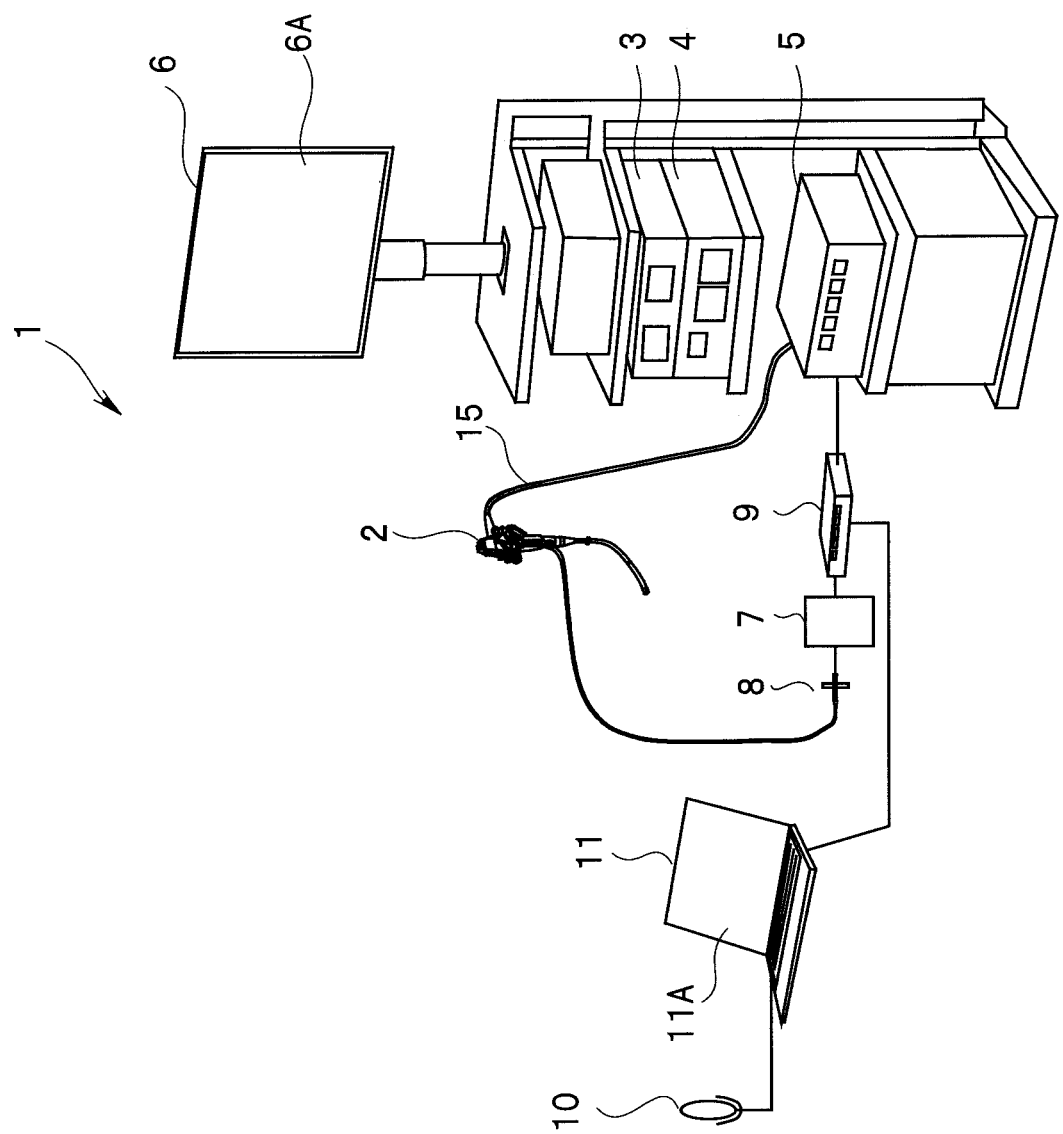
FIG. 1 is a view illustrating an example of an overall configuration of an endoscopic system according to a first embodiment of the present invention.

FIG. 1 is a view illustrating an example of an overall configuration of an endoscopic system according to a first embodiment of the present invention. As illustrated in FIG. 1, an endoscopic system 1 of the present embodiment includes an endoscope 2, a light source device 3, a video processor 4, a gas feeding device 5, and a display device 6. The endoscopic system 1 also includes a pressure sensor 7, a pressure measuring probe 8, a signal conversion device 9, a microphone 10, and a measurement data processor 11.

The endoscope 2 has an elongated insertion portion to be inserted into a body cavity. A light guide cable (not illustrated), which transmits illumination light, is inserted in the insertion portion. A rear end of the light guide cable is removably connected to the video processor 4, and transmits illumination light supplied from the light source device 3 so that a subject, such as the inside of a body cavity, is illuminated from a distal end face attached to an illumination window (not illustrated) provided at a distal end portion of the endoscope 2 via an illumination lens.

The video processor 4 as an endoscopic image processing device is electrically connected to the display device 6 that displays an endoscopic image, and processes an image pickup signal obtained through photoelectric conversion with image pickup means, such as a CMOS sensor 24, mounted on the endoscope 2, and then outputs the resulting signal as a video signal to the display device 6.

The gas feeding device 5 feeds a gas supplied from a gas supply source (not illustrated; for example, a carbon dioxide gas cylinder) to a portion to be tested in the body cavity via a gas feeding tube 51 inserted in a universal cable 15 connected to the endoscope 2. The feed flow rate of the gas from the gas feeding device 5 is outputted to the measurement data processor 11 via the signal conversion device 9.

The display device 6 as a display control device includes a display unit 6A that displays an endoscopic image received from the video processor 4 and a test information image received from the measurement data processor 11 described below. The display unit 6A can display the endoscopic image and the test information image in a superposed manner.

The pressure sensor 7 as a pressure measuring unit measures the pressure of a portion to be tested in the body cavity via the pressure measuring probe 8. A measurement result of the pressure sensor 7 is outputted to the measurement data processor 11 via the signal conversion device 9. The pressure measuring probe 8 is a disposable probe with a filter, and is used by being replaced with a new one each time a test is performed. Note that for the pressure measuring probe 8, it is also possible to use a conventionally used pressure measuring probe by attaching a disposable filter to the probe. In such a case, since it is only necessary to replace the filter each time a test is performed, an endoscopic system with an inexpensive configuration can be implemented.

The microphone 10 as a sound pressure measuring unit collects a sound uttered by a test subject under test. For example, when the test subject is tested for gastroesophageal reflux disease, a sound uttered from the mouth cavity of the test subject (i.e., a burp sound) is monitored. The sound data collected with the microphone 10 is outputted to the measurement data processor 11.

The measurement data processor 11 as a measurement data processing device performs predetermined signal processing on the feed flow rate of the gas as well as the on/off switch timing of the gas feeding received from the gas feeding device 11, the pressure of the portion to be tested received from the pressure sensor 7, and the sound data received from the microphone 10, and then generates a test information image. The test information image is displayed on a measurement result display unit 11A, and is also outputted to the display device 6.

Figure 2:
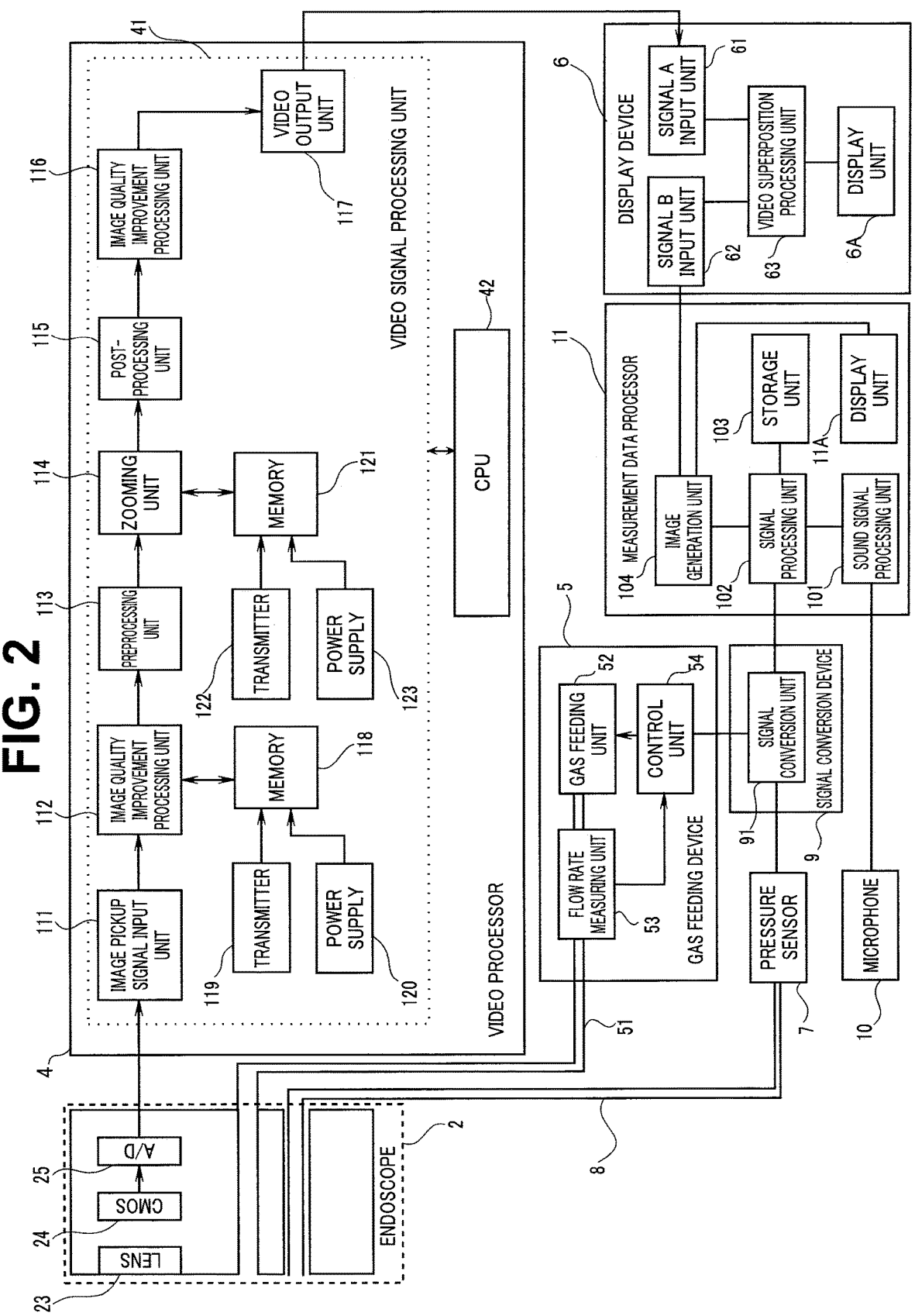
FIG. 2 is a block diagram illustrating an example of a functional configuration of the endoscopic system.

FIG. 2 is a block diagram illustrating an example of a functional configuration of the endoscopic system. Hereinafter, the detailed configuration of each device forming the endoscopic system 1 will be described with reference to FIG. 2.

The distal end portion of the endoscope 2 is provided with an observation window (not illustrated) adjacent to the illumination window. A lens 23 as an objective optical system is attached to the observation window. The CMOS sensor 24, for example, is disposed as a solid-state image pickup device at the imaging position of the lens 23. The CMOS sensor 24 performs photoelectric conversion on an optical image obtained through imaging, and thus generates an image pickup signal. The image pickup signal is converted into a digital signal via an A/D conversion unit 25, and is then outputted to the video processor 4. The gas feeding tube 51 inserted in the universal cable 15 connected to the endoscope 2 is inserted through a gas feeding channel 26 provided at the distal end portion. Thus, a gas is fed into the body cavity from the distal end portion of the endoscope 2 via the gas feeding tube 51. The endoscope 2 is also provided with a treatment instrument channel 27, and the pressure measuring probe 8 is inserted in the treatment instrument channel 27. Thus, pressure in the body cavity can be measured from the distal end portion of the endoscope 2.

The video processor 4 is electrically connected to the display device 6 that displays an endoscopic image and the like, and processes an image pickup signal obtained through photoelectric conversion with the image pickup means, such as the CMOS sensor 24, mounted on the endoscope 2, and then outputs the resulting signal as a video signal to the display device 6. The video processor 1 includes a video signal processing unit 41 and a CPU 42 as a control unit.

The video signal processing unit 41 performs various image processing on the image pickup signal received from the endoscope 2 to generate a video signal that can be displayed on the display device 6, and then outputs the video signal. The video signal processing unit 41 is connected to the CPU 42, and performs various processing according to a control instruction from the CPU 42.

The video signal processing unit 41 includes an image pickup signal input unit 111, a first image quality improvement processing unit 112, a preprocessing unit 113, a zooming unit 114, a post-processing unit 115, a second image quality improvement processing unit 116, and a video output unit 117. An image pickup signal outputted from the endoscope 2 is inputted to the image pickup signal input unit 111, and is subjected to predetermined image processing while sequentially passing through the aforementioned units, and is then outputted to the display device 6 from the video output unit 117.

The image quality improvement processing unit 112 performs an image quality improvement process having no influence on the basic image output. For example, the image quality improvement processing unit 112 performs a defect correction process for an imager, a noise reduction process, and a freezing process. The image quality improvement processing unit 112 is connected to a memory 118, and performs various processing using parameters or information stored in the memory 118.

For example, when a defect correction process is performed with the image quality improvement processing unit 112, defective pixel information and correction information, such as a correction factor, are stored in the memory 118. The image quality improvement processing unit 112 performs, based on the defective pixel information and the correction factor read from the memory 118, correction or interpolation for pixel values of a white defective pixel and pixels around the white defective pixel included in a digital video signal received from the image pickup signal input unit 111.

When a noise reduction process is performed, noise in the video signal is reduced using a parameter corresponding to a noise reduction level stored in the memory 118. Specifically, a temporal averaging process is performed with a configuration parameter read from the memory 118 using a video signal of one frame (or one field) earlier and a video signal of the current frame (or field) so that random noise in the image is reduced.

When a freezing process is performed, video signals for a plurality of frames starting from the current frame are stored in the memory 118. Then, a video signal of one frame with the best image quality is selected from among the plurality of frames stored in the memory 118 so that the selected video signal is outputted as a frozen image (i.e., a still image).

Note that a power supply 120 for supplying a drive voltage and a transmitter 119 for generating and supplying a predetermined drive frequency are connected to the memory 118.

The preprocessing unit 113 performs various image processing necessary for the basic image output, such as a white balance process, a color matrix process, and a gamma process, on the video signal subjected to various processing with the image quality improvement processing unit 112.

The zooming unit 114 performs a zooming process on the video signal subjected to various image processing with the preprocessing unit 113 according to a magnification designated by a user. The zooming unit 114 is connected to a memory 121, and performs a zooming process using parameters or information stored in the memory 121. The memory 121 can also be used to temporarily store a frame video when a zooming process is performed. Note that a power supply 123 for supplying a drive voltage and a transmitter 122 for generating and supplying a predetermined drive frequency are connected to the memory 121.

The post-processing unit 115 performs various image processing necessary for the basic image output, such as a color tone adjustment process, on the video signal subjected to a zooming process as appropriate with the zooming unit 114.

The image quality improvement processing unit 116 performs an image quality improvement process having no influence on the basic image output. For example, the image quality improvement processing unit 116 performs a structure emphasizing process. Note that a memory may also be connected to the image quality improvement processing unit 116 as appropriate so that information necessary for the process may be stored in the memory.

A video signal, which has been subjected to various image processing with the respective processing units of from the image quality improvement processing unit 112 to the image quality improvement processing unit 116, is converted into a signal that can be displayed on the display device 6 by the video output unit 117, and is then outputted to the display device 6.

The video signal processing unit 41 is connected to the CPU 42, and the operation of each unit of the video signal processing unit 41 is controlled by the CPU 42. Note that the content of specific image processing performed by each unit of the video signal processing unit 41 is not limited to the aforementioned example. For example, other processes, such as a dimming process, may be added as appropriate. The order of the individual image processing is not limited to the aforementioned example, either, and the order may be changed within a possible range.

The gas feeding device 5 includes a gas feeding unit 52, a flow rate measuring unit 53, and a control unit 54. The gas feeding unit 52 is provided with a primary decompressor, a secondary decompressor, and a flow rate control valve, which are connected in this order by a gas feeding conduit formed of silicone or fluorine resin, for example. A gas supplied from the gas supply source (not illustrated) passes through the primary decompressor, the secondary decompressor, and the flow rate control valve in this order through the gas feeding conduit so that the gas is adjusted to have a predetermined pressure and flow rate. Then, the gas is discharged from the gas feeding tube 51 via the flow rate measuring unit 53.

The control unit 54 controls the flow rate control valve provided in the gas feeding unit 52 so as to adjust the flow rate of the gas to be fed to the endoscope 2 to a predetermined value. The flow rate control valve is a type of electromagnetically driven valve, and is constructed of a control valve in which an electromagnetic coil is used for a drive portion. When a current is flowed through the electromagnetic coil, a magnetic force is generated, which in turn attracts a plunger and thus opens or closes the valve. The position of the plunger is controlled based on the amount of a current flowed through the electromagnetic coil so that the opening degree of the valve portion is controlled and the flow rate of the gas flowed through the gas feeding conduit is adjusted to a predetermined value. The control unit 54 feeds back a measurement result of the flow rate measuring unit 53 so that the opening degree of the valve portion is adjusted. The flow rate of the gas fed into the body cavity, which is the measurement result of the flow rate measuring unit 53, is outputted to the signal conversion device 9 via the control unit 54. Information on the on/off switch timing of the gas feeding is also outputted to the signal conversion device 9 from the control unit 54.

The signal conversion device 9 includes a signal conversion unit 91. The signal conversion unit 91 converts the feed flow rate of the gas as well as the information on the on/off switch timing received from the gas feeding device 5 and the pressure in the body cavity received from the pressure sensor 7 into a signal that can be subjected to data processing with the measurement data processor 11, and outputs the resulting signal. Note that the signal conversion device 9 may be provided in the information processing device 11.

The measurement data processor 11 includes a sound signal processing unit 101, a signal processing unit 102, a storage unit 103, an image generation unit 104, and a display unit 11A. The sound signal processing unit 101 converts sound data (i.e., a sound waveform signal) received from the microphone into sound pressure data (i.e., numeric data). The sound pressure data is outputted to the signal processing unit 102. The signal processing unit 102 analyzes the measurement data (i.e., the feed flow rate of the gas, the information on the on/off switch timing of the gas feeding, and the pressure in the body cavity) received in time series from the signal conversion device 101, and the sound pressure data received in time series from the sound signal processing unit 101, and then calculates the maximum value of each piece of data and calculates various types of data needed for an operator to perform diagnosis. The data inputted to the signal processing unit 102 and the data generated by the signal processing unit 102 are stored in the storage unit 103, and are also outputted to the image generation unit 104.

Figure 3:
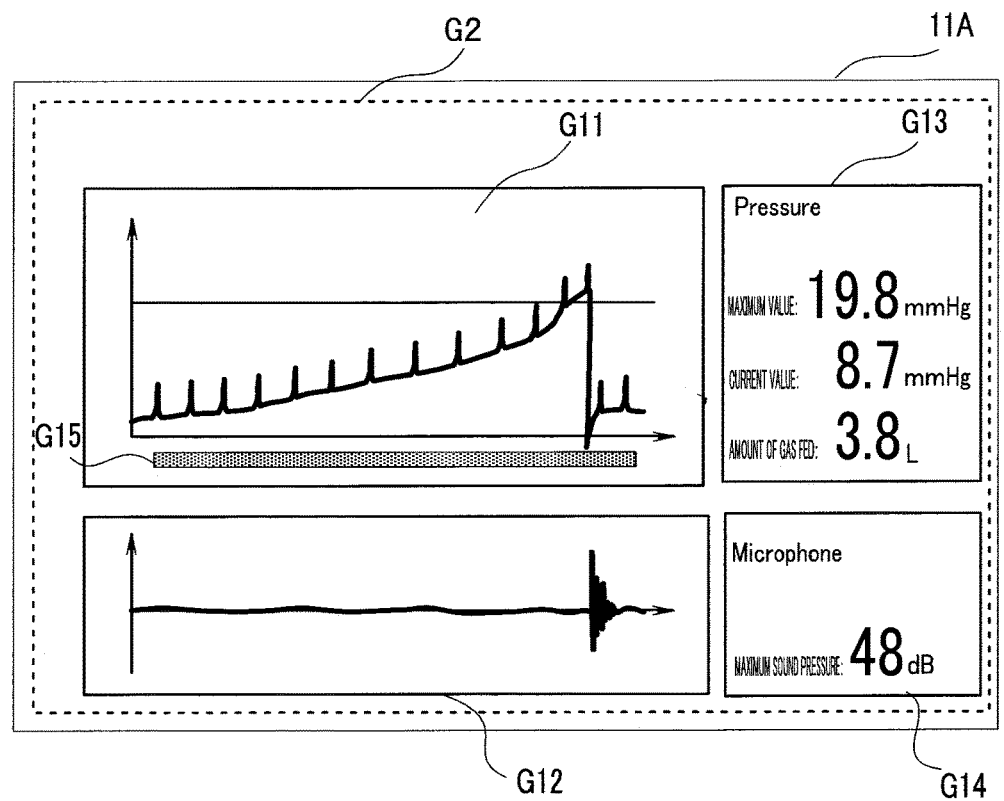
FIG. 3 is a view illustrating an example of a test information image.

The image generation unit 104 generates a test information image to be displayed on the display unit 11A based on the various types of received data. FIG. 3 is a view illustrating an example of the test information image. A test information image G2 displayed on the display unit 11A is divided into a plurality of areas. Each area displays a numerical value or a graph based on the measurement data inputted to the image generation unit 104. In the example illustrated in FIG. 3, the test information image G2 is divided in two areas in the longitudinal direction of the screen, and is also divided in two areas in the lateral direction, that is, the test information image G2 is divided into four areas.

The two areas located in the upper part of the screen display the measurement data on the pressure in the body cavity. In other words, the two areas display the measurement data (i.e., the feed flow rate of the gas and the pressure in the body cavity) received in time series from the signal conversion device 101. Specifically, the area located in the upper left part of the screen displays a graph (i.e., a pressure transition graph G11) showing temporal changes in the pressure in the body cavity, and information on the gas feeding (i.e., a range crossbar graph G15 showing the duration of gas feeding from the timing when the gas feeding is switched on to the timing when the gas feeding is switched off). Note that an identical time axis is used for a time axis that is the horizontal axis of the pressure transition graph G11 and for a time axis of the range crossbar graph G15 showing information on the gas feeding. The area located in the upper right part of the screen displays numeric data G13 on the pressure in the body cavity (e.g., the maximum value of the pressure in the body cavity up until now from the start of the gas feeding, the current value of the pressure in the body cavity, and the amount of the gas fed up until now from the start of the gas feeding).

The two areas located in the lower part of the screen display the measurement data on the sound received from the microphone 10. Specifically, the area located in the lower left part of the screen displays a sound waveform graph G12 based on the sound data (i.e., a sound waveform signal). Note that for a time axis that is the horizontal axis of the sound waveform graph G12, a time axis identical to the time axis that is the horizontal axis of the pressure transition graph G11 is used. The area located in the lower right part of the screen displays numeric data G14 on the sound pressure obtained through conversion with the sound signal processing unit 101 (e.g., the maximum sound pressure up until now). Note that the arrangement of the respective areas illustrated in FIG. 3 is only exemplary, and thus can be freely changed according to the preference of the user or considering viewability. The test information image generated by the image generation unit 104 is displayed on the display unit 11A, and is also outputted to the display device 6.

The display device 6 includes a signal A input unit 61, a signal B input unit 62, a video superposition processing unit 63, and a display unit 6A. The signal A input unit 61 receives an endoscopic video signal (i.e., endoscopic images received in time series) outputted from the video processor 4. The signal B input unit 62 receives a test information image outputted from the measurement data processor 11. The video superposition processing unit 63 superposes the endoscopic image received from the signal A input unit 61 and the test information image received from the signal B input unit in a temporally synchronized manner, thereby generating a superposition image. Note that the video superposition processing unit 63 may also select one of the image received from the signal A input unit 61 and the image received from the signal B input unit 62, and output the selected image to the display unit 6A. In other words, the video superposition processing unit 63 outputs one of the superposition image obtained by superposing the endoscopic image and the test information image, the endoscopic test image, and the test information image to the display unit 6A. An image to be outputted to the display unit 6A from the video superposition processing unit 63 can be designated by a tester.

Figure 4:
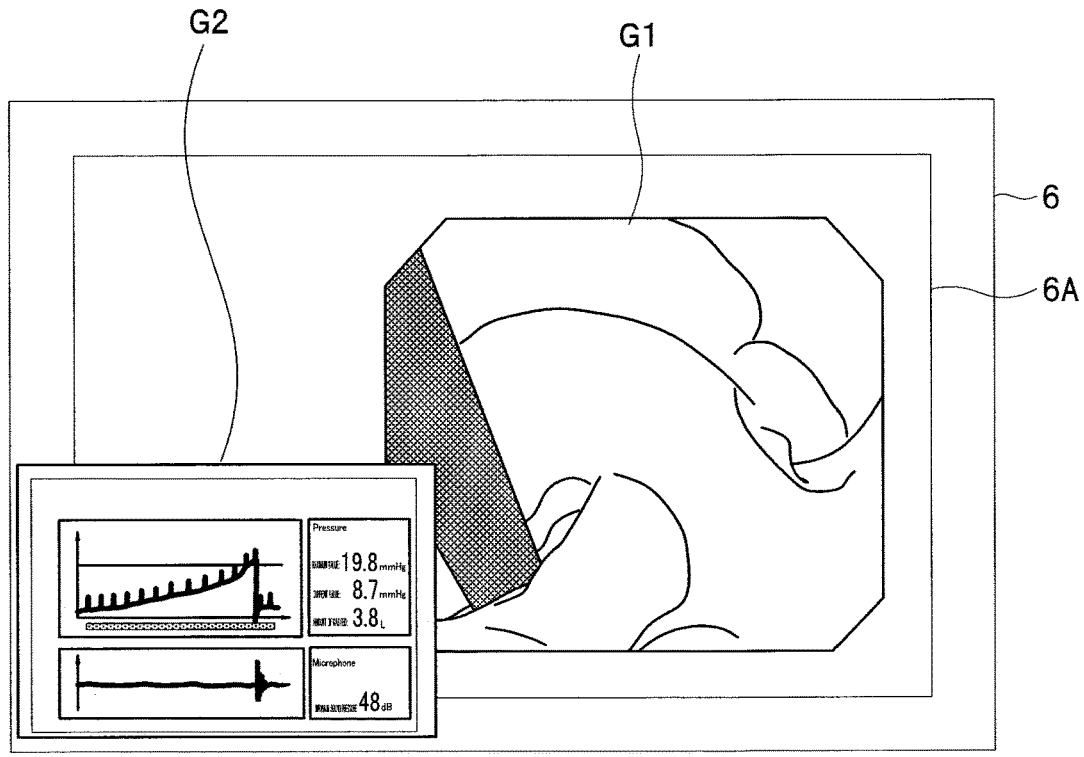
FIG. 4 is a view illustrating an example of a superposition image obtained by superposing an endoscopic image and a test information image.

FIG. 4 is a view illustrating an example of the superposition image obtained by superposing the endoscopic image and the test information image. The superposition image illustrated in FIG. 4 is an example of the image displayed on the display unit 6A of the display device 6. As illustrated in FIG. 4, when an endoscopic image G1 and the test information image G2 are displayed in a superposed manner, the test information image G2 is preferably displayed in a smaller region than the region of the endoscopic image G1. This is because the main objective of the display unit 6A of the display device 6 is to observe the relaxed state of the lower esophageal sphincter (LES) of the cardiac part of the stomach on the endoscopic image G1 and also because the test information image G2 is also displayed on the display unit 11A of the measurement data processor 11 and thus the test information image G2 displayed on the display unit 6A is used as auxiliary information.

Note that since the test information image G2, which is displayed on the display unit 4A of the display device 6, is displayed temporally synchronously with the endoscopic image G1, it is possible to recognize at first sight the various types of measurement data (i.e., the measurement data on the pressure in the body cavity) and the sound data on the sound (i.e., a burp sound) uttered from the mouth cavity of the test subject at a time point when the endoscopic image G1 is picked up. For example, when it is observed on the endoscopic image G1 that the state of the lower esophageal sphincter (LES) of the cardiac part of the stomach has changed from the contracted state to the relaxed state, it is possible to promptly diagnose the test subject as having gastroesophageal reflux disease (hereinafter referred to as GERD) by also observing changes in the pressure in the body cavity and the presence or absence of a burp sound.

The test information image G2 illustrated in FIG. 3 and the superposition image illustrated in FIG. 4 are examples of a test image of a healthy subject. When a healthy subject is tested, the valve of the cardiac part is in a closed state on the endoscopic image G1 immediately after the start of the gas feeding, but when the gas feeding is continued, the valve opens at a certain time point, and the state of the lower esophageal sphincter (LES) changes from the contracted state to the relaxed state. Meanwhile, pressure in the body cavity gradually increases from the time immediately after the start of the gas feeding, but decreases at once at a time point when the valve of the cardiac part opens. Further, regarding a sound uttered from the mouth cavity of the test subject, a silent state is continued from the time immediately after the start of the gas feeding, but a big gas release sound is uttered at a time point when the valve of the cardiac part opens.

Figure 5:
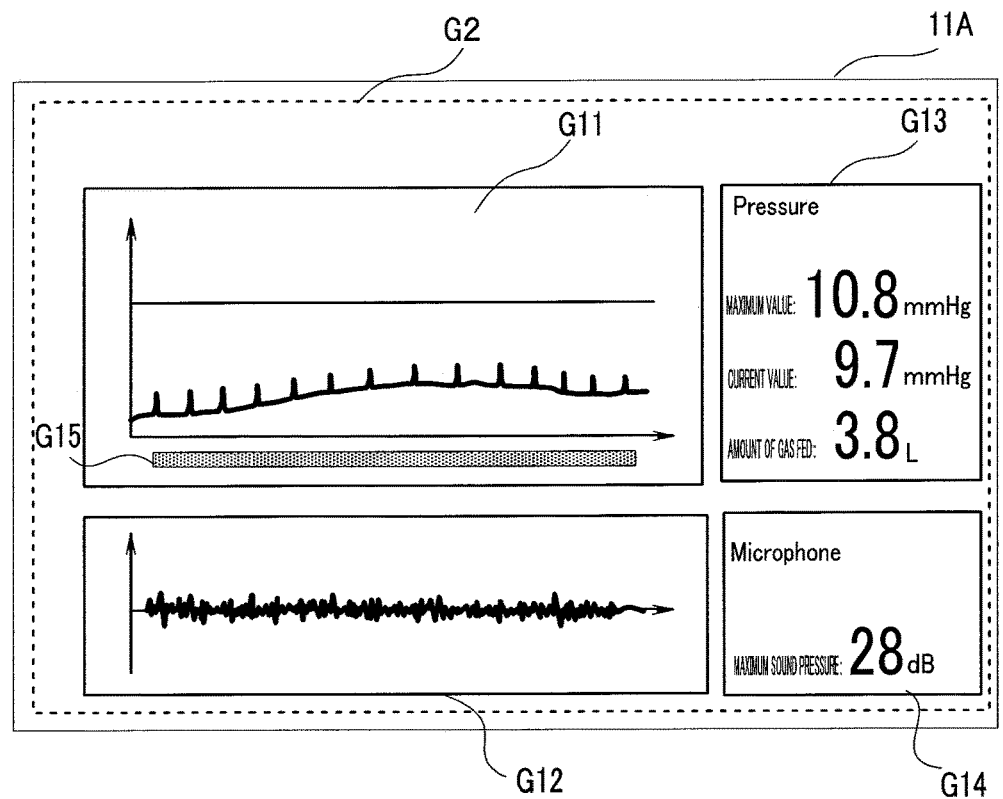
FIG. 5 is a view illustrating an example of a test information image.
Figure 6:
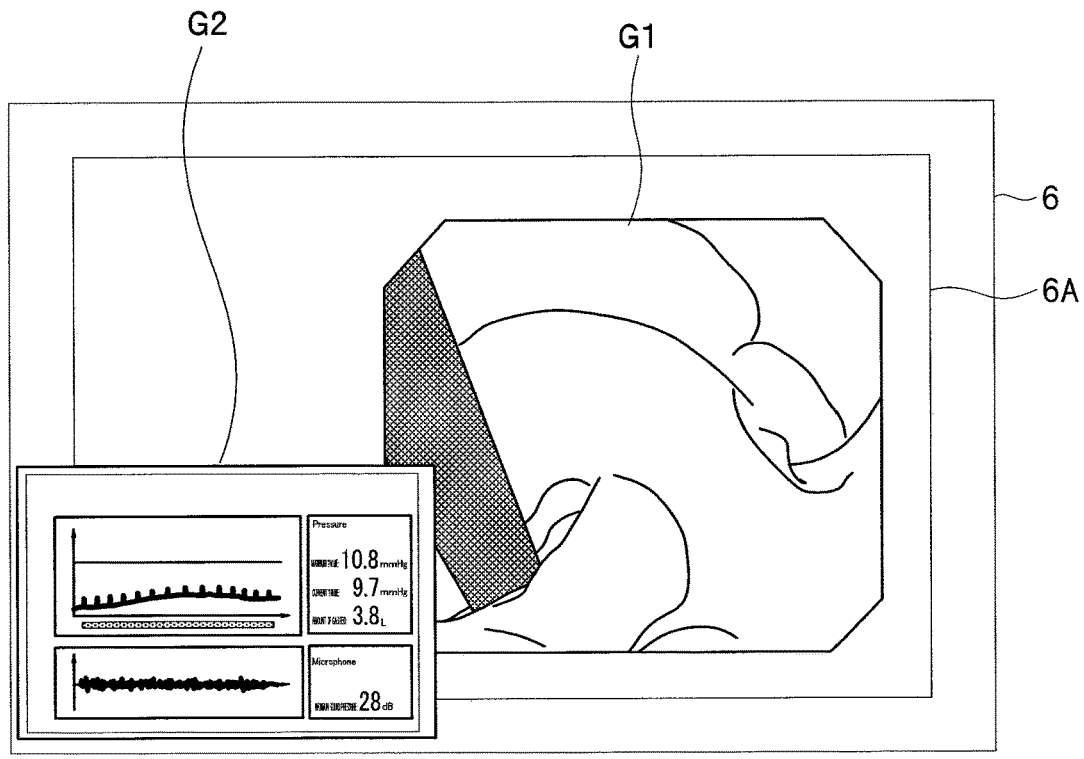
FIG. 6 is a view illustrating an example of a superposition image obtained by superposing an endoscopic image and a test information image.

FIG. 5 is a view illustrating an example of the test information image. FIG. 6 is a view illustrating an example of the superposition image obtained by superposing the endoscopic image and the test information image. Each of FIGS. 5 and 6 illustrates an example of an image when a patient with GERD is tested. When a patient with GERD is tested, the valve of the cardiac part is loosely open on the endoscopic image G1 from the time immediately after the start of the gas feeding, and even when the gas feeding is continued, almost no change is seen in the relaxed state of the lower esophageal sphincter (LES). In addition, almost no change is seen in the pressure in the body cavity from the time immediately after the start of the gas feeding, either, and thus, a sudden increase or decrease in the pressure is not seen. Further, regarding a sound uttered from the mouth cavity of the test subject, a release sound that is always low and weak is uttered from the time immediately after the start of the gas feeding.

As described above, the endoscopic system of the present embodiment can acquire an endoscopic image of a portion to be tested with the endoscope 2 and the video processor 4 while feeding a gas to the cardiac part of the stomach, which is a portion to be observed, and acquire pressure in the body cavity of the portion to be tested with the pressure sensor 7, and further acquire sound data uttered from the mouth cavity of the test subject with the microphone 10. With the measurement data processor 11, the test information image G2 is generated by temporally synchronizing temporal changes in the pressure in the body cavity, temporal changes in the sound data, and information on the gas feeding. Further, by temporally synchronizing the endoscopic image G1 with the test information image G2 and displaying information necessary for diagnosis on the display device 6 in an integrated manner, it is possible to allow a tester to promptly obtain a result of the diagnosis. Furthermore, since a test can be performed in a short time, the burden on the patient can be reduced.

Note that the endoscopic system of the present embodiment can be used for not only the aforementioned test of the cardiac part of the stomach for diagnosing GERD, but also a test for the relaxed state of the anal sphincter, the urethral sphincter, and the like.

Figure 7:
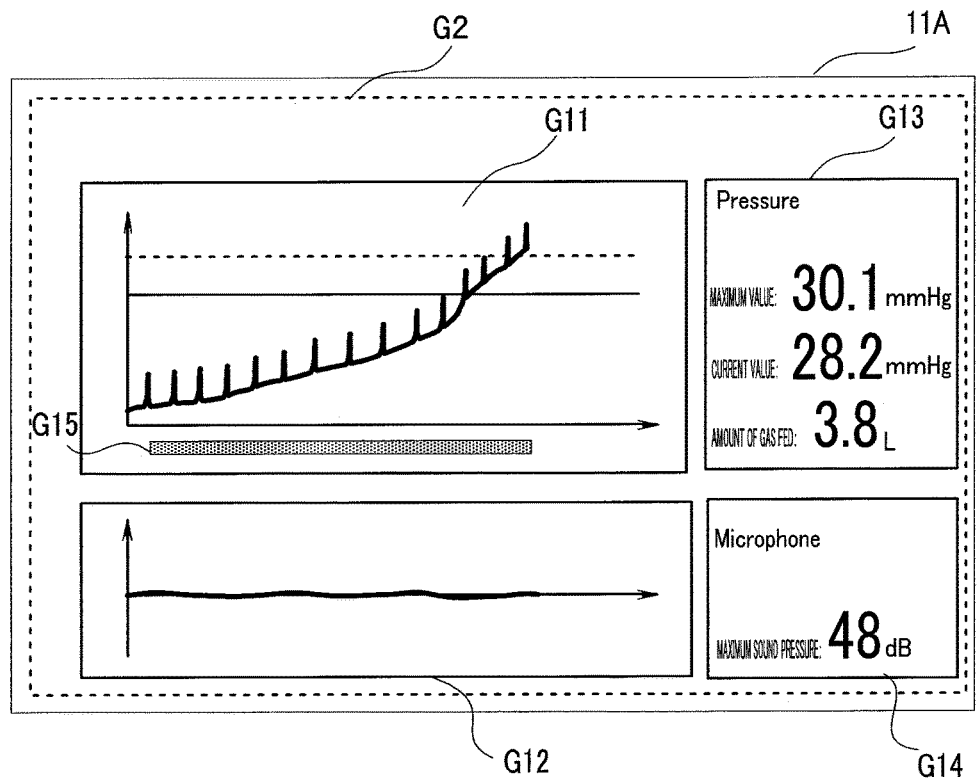
FIG. 7 is a view illustrating an example of a test information image in a state where a gas is overfed.

To prevent overfeeding of a gas into a body cavity, a threshold pressure may be set in advance for pressure in the body cavity so that when the measured value of the pressure sensor 7 has become greater than or equal to the threshold pressure during a test, a warning state may be displayed on the test information image G2. FIG. 7 is a view illustrating an example of the test information image in a state where a gas is overfed. In FIG. 7, the measured value of the pressure in the body cavity in the pressure transition graph G11 is over the threshold pressure (i.e., a pressure value indicated by a dotted line in the pressure transition graph G11). In such a case, the display style of the numeric data G13 on the pressure in the body cavity is changed by, for example, changing the display color of the maximum value of the pressure in the body cavity up until now from the start of the gas feeding or the current value of the pressure in the body cavity to a color different from the usual display color, enlarging the display size, blinking the numerical value, or displaying the numerical value in bold. In this manner, displaying the test information image G2 in a manner different from the usual manner can allow a tester to recognize the danger of overfeeding of a gas and thus perform a test safely.

Note that a method for displaying the warning state is not limited to the aforementioned display method, and it is also possible to use other display methods such as displaying a warning message. It is also possible to provide a threshold for the amount or duration of gas feeding in addition to providing a threshold for the pressure in the body cavity.

Figure 8:
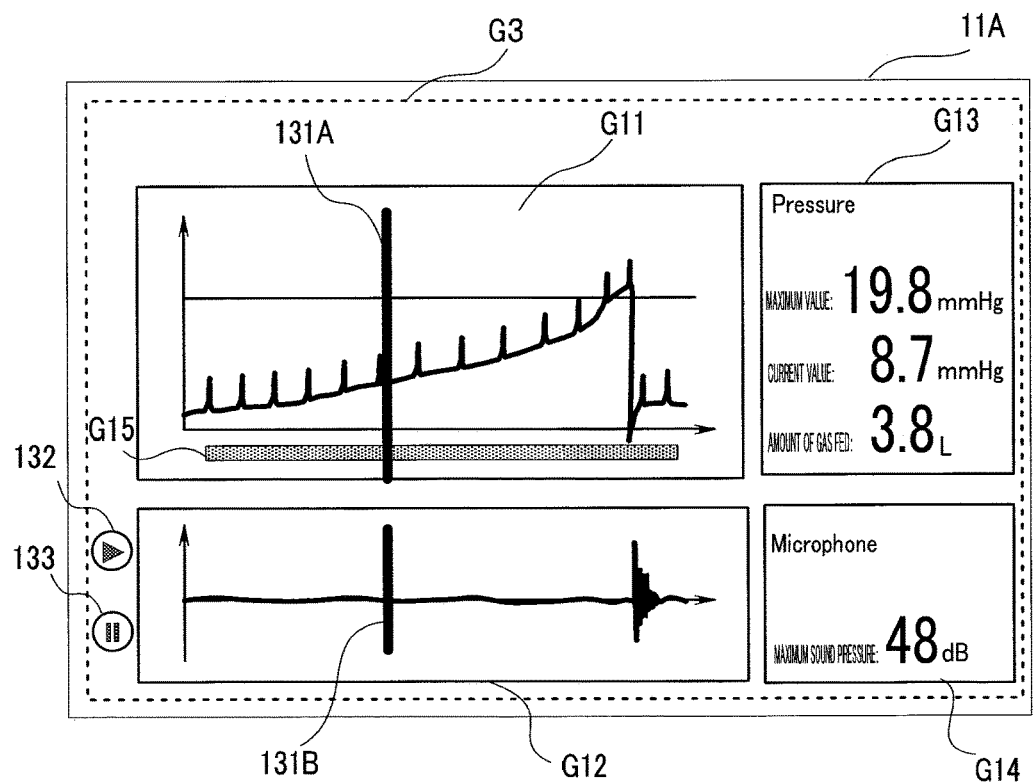
FIG. 8 is a view illustrating an example of a recorded/playback image.

The display unit 11A of the measurement data processor 11 may display not only the test information image G2 generated based on the data being acquired but also a recorded/playback image G3 generated by reading data recorded on the recording unit 103. FIG. 8 is a view illustrating an example of the recorded/playback image. The recorded/playback image G3 has a layout structure similar to the layout structure of the test information image G2. In other words, the recorded/playback image G3 is divided in two areas in the longitudinal direction of the screen, and is also divided in two areas in the lateral direction, that is, the recorded/playback image G3 is divided into four areas. The area located in the upper left part of the screen displays the pressure transition graph G11 and information on the gas feeding (i.e., the range crossbar graph G15 showing the duration of gas feeding). The area located in the upper right part of the screen displays the numeric data G13 on the pressure in the body cavity. The area located in the lower left part of the screen displays the sound waveform graph G12 based on the sound data (i.e., a sound waveform signal). The area located in the lower right part of the screen displays the numeric data G14 on the sound pressure obtained through conversion with the sound signal processing unit 101.

A play button 132 and a stop button 133 are provided in a region on the left side of the sound waveform graph G12. Cursors 131A and 131B are respectively displayed in the pressure transition graph G11 and the sound waveform graph G12. In other words, as the play button 132 is pressed, the cursors 131A and 131B move to the right side on the time axes of the graphs with the passage of time, and also, numeric data on the pressure in the body cavity and numeric data on the sound pressure corresponding to the time where the cursors 131A and 131B are located are displayed in predetermined areas. When the stop button 133 is pressed, the movement of the cursors 131A and 131B stops. Note that the cursors 131A and 131B may be not only moved or stopped with the play button 132 or the stop button 133 but also moved to a desired time position by a tester through a drag operation or the like. Note that the tester can select the image to be displayed on the display unit 11A by appropriately switching between the test information image G2 and the recorded/playback image G3.

While the recorded/playback image G3 is displayed on the display unit 11A, the endoscopic image G1 acquired at the time where the cursors 131A and 131B are located may be read from a storage unit (not illustrated) of the video processor 4, and displayed on the display unit 6A of the display device 6. According to such a configuration, the tester can perform observation while temporally synchronizing the measurement data with the endoscopic image after testing. Thus, analysis of data for diagnosis can be performed precisely, and the accuracy of the diagnosis can thus be improved.

Note that various types of measurement data recorded on the recording unit 103 and endoscopic images recorded on the storage unit (not illustrated) of the video processor 4 may be not only displayed on the display device 6 but also outputted to an external database or analysis device through wire communication, wireless communication, or a recording medium, such as a USB. The superposition image obtained by superposing the test information image G2 and the endoscopic image G1 and the superposition image obtained by superposing the recorded/playback image G3 and the endoscopic image G1 may be stored as image data or outputted to an external device.

Second Embodiment

In the foregoing first embodiment, the gas feeding device 5 transmits information on the gas feeding to the measurement data processor 11. In contrast, the present embodiment differs from the first embodiment in that the gas feeding device 5 does not input any information to the measurement data processor 11.

Figure 9:
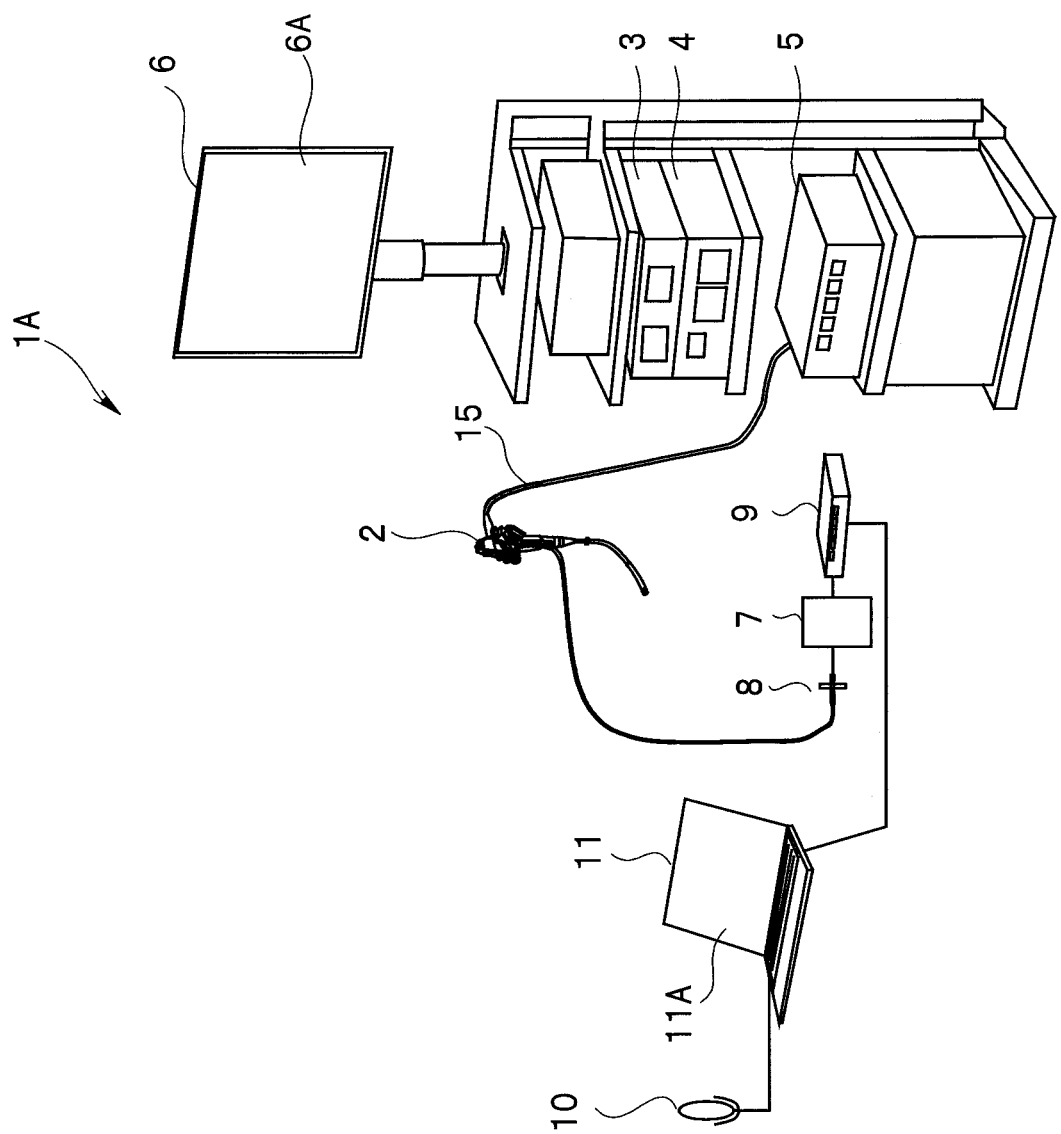
FIG. 9 is a view illustrating an example of an overall configuration of an endoscopic system according to a second embodiment.

FIG. 9 is a view illustrating an example of an overall configuration of an endoscopic system according to the second embodiment. Components of an endoscopic system 1A of the present embodiment are similar to the components of the endoscopic system 1 of the first embodiment illustrated in FIG. 1. However, the second embodiment differs from the first embodiment in that the gas feeding device 5 and the signal conversion device 9 are not connected. For the pressure measuring probe 8, it is possible to use a disposable probe with a filter and replace the probe with a new one each time a test is performed as in the first embodiment, or it is also possible to use a conventionally used pressure measuring probe by attaching a disposable filter to the probe. The signal conversion unit 9 converts pressure in the body cavity received from the pressure sensor 7 into a signal that can be subjected to data processing with the measurement data processor 11, and outputs the resulting signal. The other components are denoted by the same reference signs as the reference signs of the first embodiment, and the description of such components is omitted.

Figure 10:
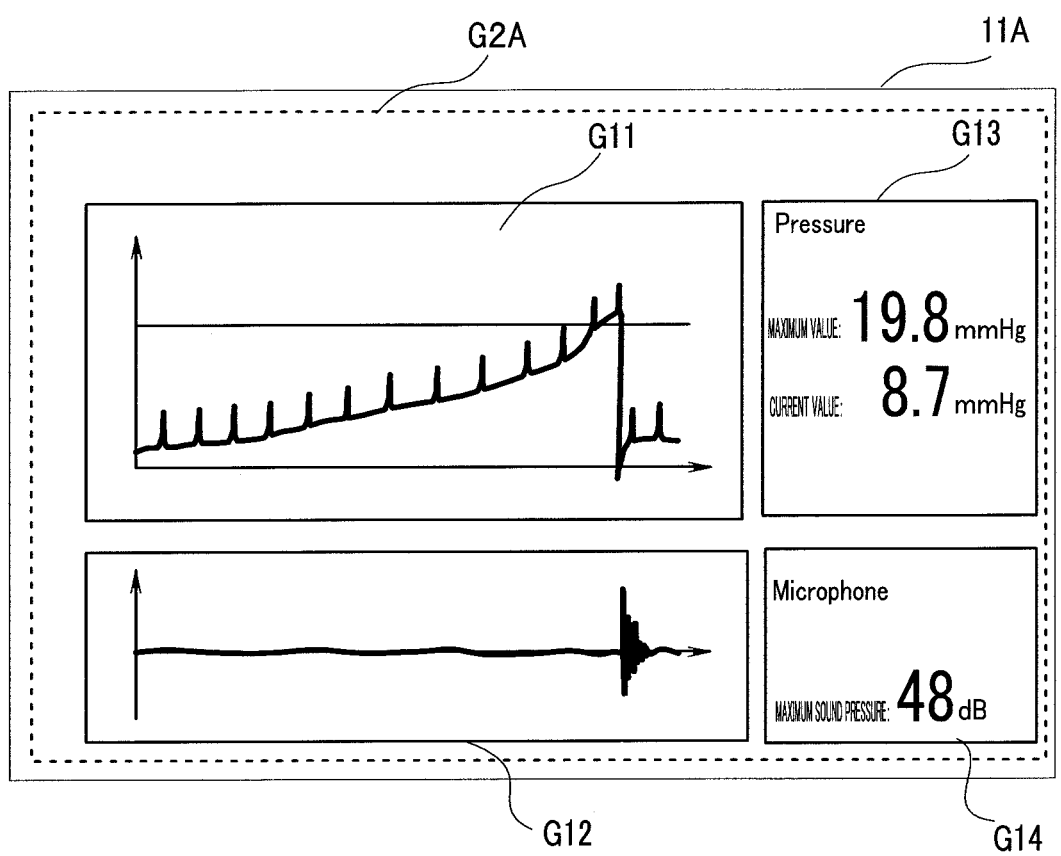
FIG. 10 is a view illustrating an example of a test information image according to the second embodiment.

FIG. 10 is a view illustrating an example of a test information image according to the second embodiment. When a test for GERD is performed with an endoscopic system such as the one illustrated in FIG. 9, a test information image G2A displayed on the display unit 11A of the measurement data processor 11 is similar to the test information image G2 of the first embodiment illustrated in FIG. 3 except that the range crossbar graph G15, which shows the duration of gas feeding, is not displayed and that the amount of the gas fed up until now from the start of the gas feeding is not displayed as the numeric data G13 on the pressure in the body cavity although the maximum value of the pressure in the body cavity up until now from the start of the gas feeding and the current value of the pressure in the body cavity are displayed. In other words, in the endoscopic system 1A of the present embodiment, since information on the gas feeding (i.e., information on the feed flow rate of the gas and the on/off switch timing) is not inputted to the measurement data processor 11 from the gas feeding device 5, an image related to such information is not generated, and the test information image G2A such as the one illustrated in FIG. 10 is generated and displayed. Note that the second embodiment is similar to the first embodiment in that the test information image G2A is generated by temporally synchronizing temporal changes in the pressure in the body cavity with temporal changes in the sound data. The second embodiment is also similar to the first embodiment in that a superposition image is generated by temporally synchronizing the endoscopic image G1 with the test information image G2A with the video superposition processing unit 63 of the display device 6 and the resulting superposition image is displayed on the display unit 6A.

As described above, the endoscopic system 1A of the present embodiment can acquire an endoscopic image of a portion to be tested with the endoscope 2 and the video processor 4 while feeding a gas to the cardiac part of the stomach as a portion to be observed, and acquire pressure in the body cavity of the portion to be tested with the pressure sensor 7, and further acquire sound data uttered from the mouth cavity of the test subject with the microphone 10. With the measurement data processor 11, the test information image G2A is generated by temporally synchronizing temporal changes in the pressure in the body cavity with temporal changes in the sound data. Further, by temporally synchronizing the endoscopic image G1 with the test information image G2A and displaying information necessary for diagnosis on the display device 6 in an integrated manner, it is possible to allow a tester to promptly obtain a result of the diagnosis. Furthermore, since a test can be performed in a short time, the burden on the patient can be reduced.

Third Embodiment

In the foregoing second embodiment, sound data uttered from the mouth cavity of the test subject is acquired with the microphone 10, and the sound data is transmitted to the measurement data processor 11. In contrast, an endoscopic system 1B of the present embodiment differs from the endoscopic system of the second embodiment in that a microphone is not provided.

Figure 11:
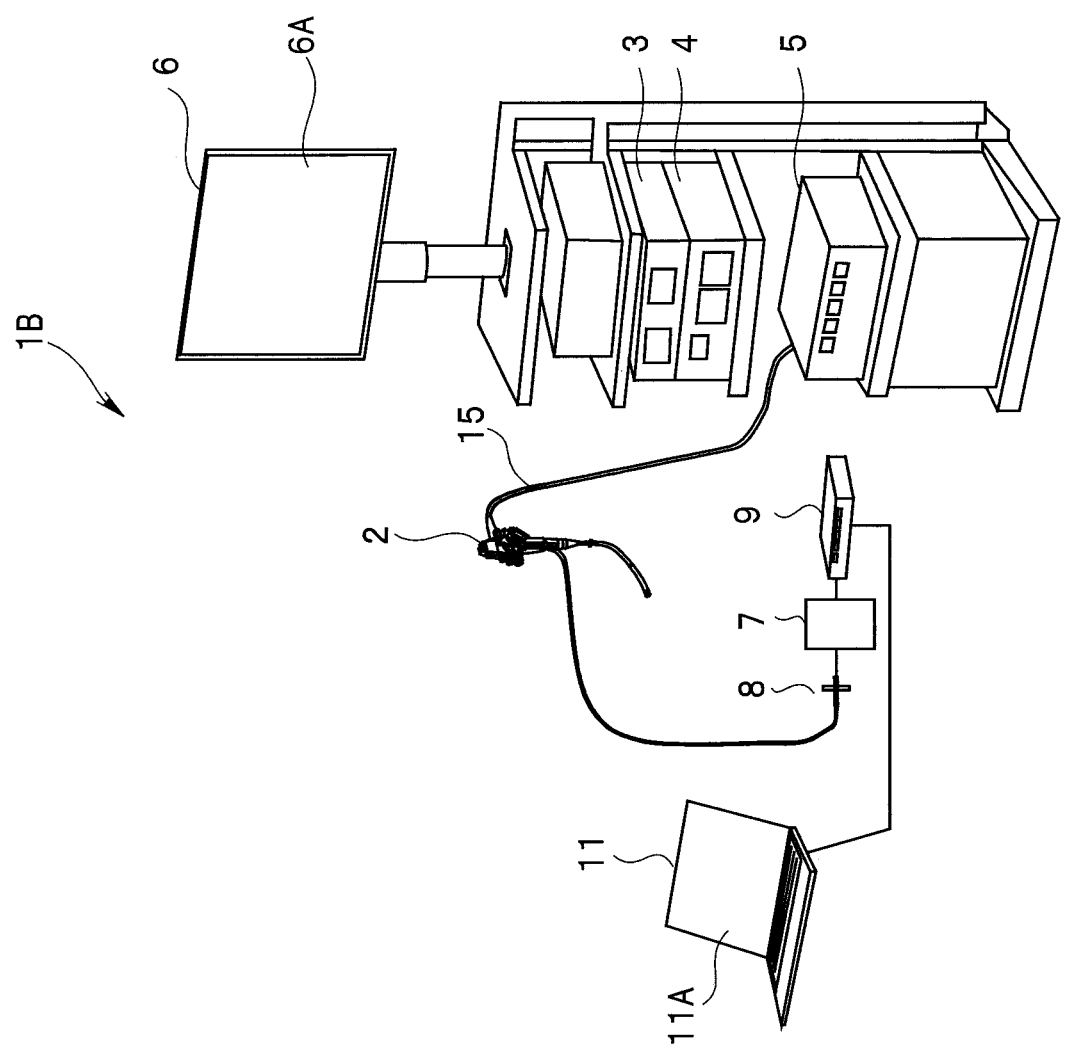
FIG. 11 is a view illustrating an example of an overall configuration of an endoscopic system according to a third embodiment.

FIG. 11 is a view illustrating an example of an overall configuration of the endoscopic system according to the third embodiment. Components of the endoscopic system 1B of the present embodiment correspond to the components of the endoscopic system 1A of the second embodiment illustrated in FIG. 9 except that the microphone 10 is removed. For the pressure measuring probe 8, it is possible to use a disposable probe with a filter and replace the probe with a new one each time a test is performed as in the second embodiment, or it is also possible to use a conventionally used pressure measuring probe by attaching a disposable filter to the probe. Since a microphone is not provided, the measurement data processor 11 is not provided with the sound signal processing unit 101. The measurement data processor 11 analyzes pressure in the body cavity received from the pressure sensor 7 via the signal conversion unit 9, and then calculates the maximum value of each piece of data and calculates various types of data needed for an operator to perform diagnosis. The other components are denoted by the same reference signs as the reference signs of the second embodiment, and the description of such components is omitted.

Figure 12:
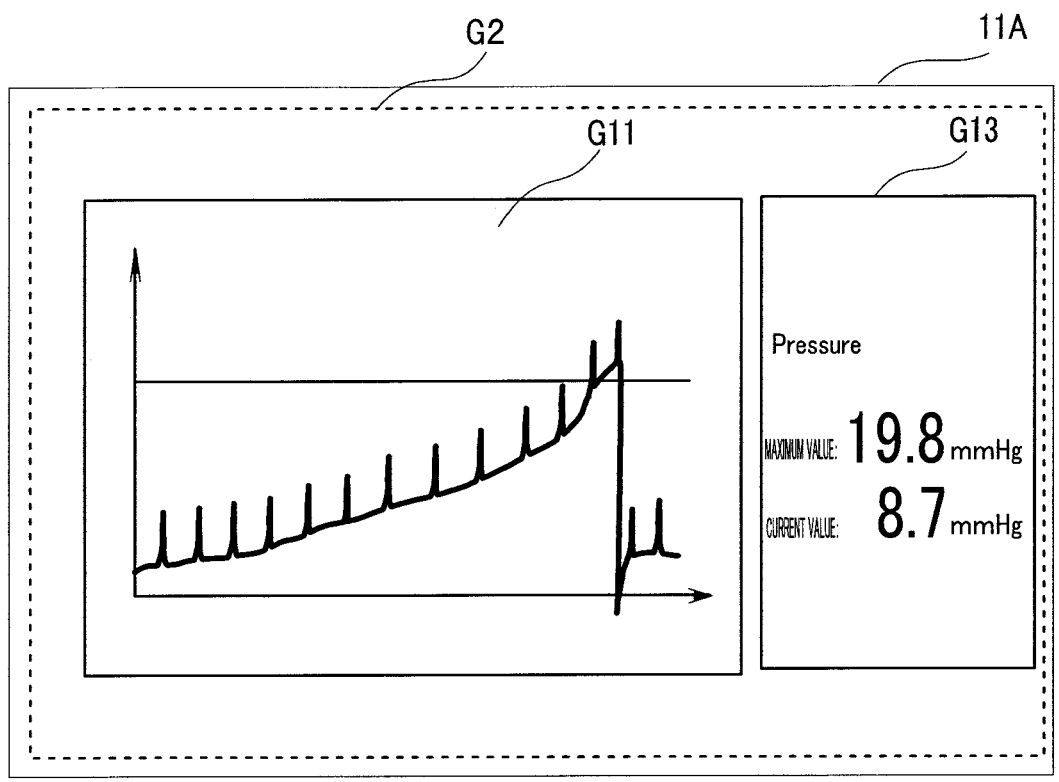
FIG. 12 is a view illustrating an example of a test information image according to the third embodiment.

FIG. 12 is a view illustrating an example of a test information image according to the third embodiment. When a test for GERD is performed with the endoscopic system 1B such as the one illustrated in FIG. 11, a test information image G2B displayed on the display unit 11A of the measurement data processor 11 is similar to the test information image G2A of the second embodiment illustrated in FIG. 310 except that the sound waveform graph G12 based on the measurement data on the sound received from the microphone 10, that is, the sound data (i.e., a sound waveform signal) and the numeric data G14 related to the sound pressure are not displayed. In other words, since the endoscopic system 1B of the present embodiment includes no microphone 10, sound data uttered from the mouth cavity of the test subject is not inputted to the measurement data processor 11. Thus, an image related to such data is not generated, and the test information image G2B such as the one illustrated in FIG. 12 is generated and displayed.

Note that the third embodiment is similar to the second embodiment in that a superposition image is generated by temporally synchronizing the endoscopic image G1 with the test information image G2B with the video superposition processing unit 63 of the display device 6 and the resulting superposition image is displayed on the display unit 6A.

As described above, the endoscopic system 1B of the present embodiment can acquire an endoscopic image of a portion to be tested with the endoscope 2 and the video processor 4 while feeding a gas to the cardiac part of the stomach as a portion to be observed, and acquire pressure in the body cavity of the portion to be tested with the pressure sensor 7. With the measurement data processor 11, the test information image G2B to be displayed is generated by converting temporal changes in the pressure in the body cavity into a graph and numerical values. Further, by temporally synchronizing the endoscopic image G1 with the test information image G2B and displaying information with a high degree of necessity among pieces of information to be used for diagnosis on the display device 6 in an integrated manner, it is possible to allow a tester to promptly obtain a result of the diagnosis. Furthermore, since a test can be performed in a short time, the burden on the patient can be reduced.

Note that information on the gas feeding (e.g., the feed flow rate of the gas and information on the on/off timing of the gas feeding) of the gas feeding device 5 may be inputted to the measurement data processor 11, and the range crossbar graph G15 may be added to the test information image G2B. As the numeric data G13 on the pressure in the body cavity of the test information image G2B, it is also possible to display the amount of the gas fed up until now from the start of the gas feeding in addition to the maximum value of the pressure in the body cavity up until now from the start of the gas feeding and the current value of the pressure in the body cavity.

Fourth Embodiment

In the foregoing first embodiment, data on the pressure in the body cavity measured with the pressure sensor 7 is transmitted to the measurement data processor 11 via the signal conversion device 9. In contrast, the present embodiment differs from the first embodiment in that data on the pressure in the body cavity is transmitted to the measurement data processor 11 via a gas feeding device 5C and that the data on the pressure in the body cavity as well as information on the gas feeding (e.g., the feed flow rate of the gas and information on the on/off timing of the gas feeding) is transmitted to the measurement data processor 11 not via the signal conversion device 9.

Figure 13:
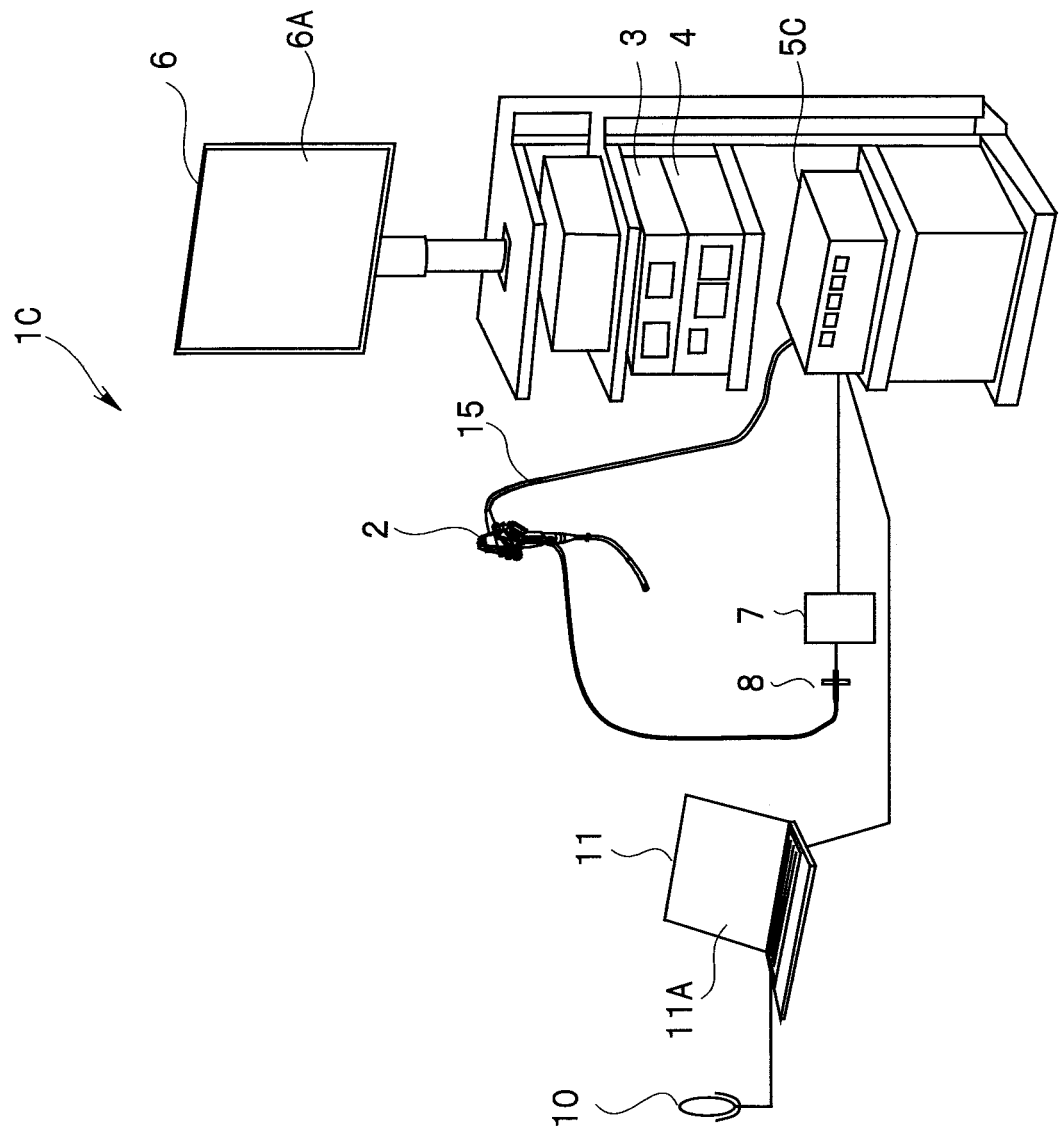
FIG. 13 is a view illustrating an example of an overall configuration of an endoscopic system according to a fourth embodiment.

FIG. 13 is a view illustrating an example of an overall configuration of an endoscopic system according to the fourth embodiment. Components of an endoscopic system 1C of the present embodiment are similar to the components of the endoscopic system 1 of the first embodiment illustrated in FIG. 1 except that the signal conversion device 9 is not disposed. Regarding the connection of the components, the endoscopic system 1C of the fourth embodiment differs from the endoscopic system 1 of the first embodiment illustrated in FIG. 1 in that the gas feeding device 5C and the measurement data processor 11 are directly connected. The fourth embodiment also differs from the first embodiment in that the pressure sensor 7 is connected to the gas feeding device 5C. For the pressure measuring probe 8, it is possible to use a disposable probe with a filter and replace the probe with a new one each time a test is performed as in the first embodiment, or it is also possible to use a conventionally used pressure measuring probe by attaching a disposable filter to the probe. The other components are denoted by the same reference signs as the reference signs of the first embodiment, and the description of such components is omitted.

FIG. 14 is a block diagram illustrating an example of a functional configuration of the endoscopic system according to the fourth embodiment. Measurement data on the pressure in the body cavity obtained with the pressure sensor 7 is inputted to the control unit 54 of the gas feeding device 5C. The control unit 54 of the gas feeding device 5C outputs to the measurement data processor 11 the feed flow rate of the gas for the body cavity, which is the measurement data of the flow rate measuring unit 53, and the measurement data on the pressure in the body cavity received from the pressure sensor 7. The control unit 54 also outputs to the measurement data processor 11 information on the on/off switch timing of the gas feeding. The other components are similar to the components of the endoscopic system of the first embodiment illustrated in FIG. 2, and thus, the description of such components is omitted. Note that a test information image generated by the measurement data processor 11 is similar to the test information image illustrated in FIG. 3, and a superposition image generated by the display device 4 is similar to the superposition image illustrated in FIG. 4.

As described above, the endoscopic system 1C of the present embodiment can acquire an endoscopic image of a portion to be tested with the endoscope 2 and the video processor 4 while feeding a gas to the cardiac part of the stomach as a portion to be observed, and acquire pressure in the body cavity of the portion to be tested with the pressure sensor 7, and further acquire sound data uttered from the mouth cavity of the test subject with the microphone 10. By outputting the pressure in the body cavity acquired with the pressure sensor 7 to the measurement data processor 11 via the gas feeding device 5, it is possible to output the feed flow rate of the gas, the information on the on/off switch timing of the gas feeding, and the pressure in the body cavity at a time, and thus, it is possible to output the pressure in the body cavity and the on/off switch timing of the gas feeding in a temporally synchronized manner Thus, it is possible to simplify the process of generating the test information image G2 by temporally synchronizing various types of inputted data.

With the measurement data processor 11, the test information image G2 is generated by temporally synchronizing temporal changes in the pressure in the body cavity with temporal changes in the sound data. Further, by temporally synchronizing the endoscopic image G1 with the test information image G2 and displaying information necessary for diagnosis on the display device 6 in an integrated manner, it is possible to allow a tester to promptly obtain a result of the diagnosis. Furthermore, since a test can be performed in a short time, the burden on the patient can be reduced.

Although several embodiments of the present invention have been described, such embodiments are only exemplary and are not intended to limit the scope of the invention. Such novel embodiments can be implemented in various other forms, and can be omitted, replaced, or changed in various ways within the gist of the invention. Such embodiments and modifications to the embodiments are included in the scope and gist of the invention, and are also included in the invention recited in the claims and equivalents of such invention.

What is claimed is:

1. An endoscopic system comprising a processor, the processor being configured to execute:
generating from a measured value of pressure in a lumen of a subject a first temporal change image that is an image showing a temporal change in the pressure in the lumen,
generating an observation image for observing an opened/closed state of a valve portion in the lumen of the subject in real time from an image pickup signal obtained by picking up an image of the opened/closed state of the valve portion in the lumen in real time using an endoscope, and
generating a first superposition image by superposing the first temporal change image and the observation image in a temporally synchronized manner.

2. The endoscopic system according to claim 1, further comprising a sound pressure measuring unit configured to measure a gas release sound released from the lumen of the subject, wherein: the processor generates from a measured value of the sound pressure measuring unit a second temporal change image that is an image showing a temporal change in the gas release sound, and generates a second superposition image by superposing the first temporal change image, the second temporal change image, and the observation image in the temporally synchronized manner.

3. The endoscopic system according to claim 1, wherein the processor clearly indicates a time period in which a gas is fed into the lumen on the first temporal change image.

4. The endoscopic system according to claim 3, wherein the processor calculates an amount of the gas fed into the lumen, and displays the amount of the gas fed on the first superposition image.

5. The endoscopic system according to claim 4, wherein the processor adds a display indicating a warning to the first temporal change image when the amount of the gas fed exceeds a preset threshold.

6. The endoscopic system according to claim 2, wherein the processor clearly indicates a time period in which a gas is fed into the lumen on the second temporal change image.

7. The endoscopic system according to claim 6, wherein the processor calculates an amount of the gas fed into the lumen, and displays the amount of the gas fed on the second superposition image.

8. The endoscopic system according to claim 7, wherein the processor adds a display indicating a warning to the first temporal change image when the amount of the gas fed exceeds a preset threshold.

9. The endoscopic system according to claim 1, further comprising a gas feeding device communicating with a gas feed source that feeds a predetermined gas, the gas feeding device being configured to feed the gas into the lumen of the subject via a gas feeding conduit provided in the endoscope, wherein: the processor includes a pressure measuring unit configured to measure pressure in the lumen of the subject.

10. The endoscopic system according to claim 1, wherein the processor includes a measurement data processing device configured to generate from the measured value of pressure in the lumen of the subject the first temporal change image that is the image showing the temporal change in the pressure in the lumen; and an endoscopic image processing device configured to generate the observation image from the image pickup signal obtained by picking up the image of inside of the lumen of the subject using the endoscope.

11. An endoscopic image display control method comprising:
generating from a measured value of pressure in a lumen of a subject a first temporal change image that is an image showing a temporal change in the pressure in the lumen;
generating an observation image for observing an opened/closed state of a valve portion in the lumen of the subject in real time from an image pickup signal obtained by picking up an image of the opened/closed state of the valve portion in the lumen in real time using an endoscope; and
generating a first superposition image by superposing the first temporal change image and the observation image in a temporally synchronized manner.

12. The endoscopic image display control method according to claim 11, further comprising: measuring a gas release sound released from the lumen of the subject; generating a second temporal change image that is an image showing a temporal change in the gas release sound; and generating a second superposition image by superposing the first temporal change image, the second temporal change image, and the observation image in the temporally synchronized manner.

13. The endoscopic image display control method according to claim 12, further comprising:
calculating an amount of a gas fed into the lumen; and
displaying the amount of the gas fed on the first superposition image.

14. The endoscopic image display control method according to claim 13, further comprising adding a display indicating a warning to the first temporal change image when the amount of the gas fed exceeds a preset threshold.

15. The endoscopic image display control method according to claim 13, further comprising clearly indicating a time period in which the gas is fed into the lumen on the second temporal change image.

16. The endoscopic image display control method according to claim 15, further comprising: calculating the amount of the gas fed into the lumen; and displaying the amount of the gas fed on the second superposition image.

17. The endoscopic image display control method according to claim 16, further comprising adding a display indicating a warning to the first temporal change image when the amount of the gas fed exceeds a preset threshold.

18. An endoscopic system comprising a processor, the processor being configured to execute: generating from a measured value of pressure in a lumen of a subject a first temporal change image that is an image showing a temporal change in the pressure in the lumen, generating an observation image for observing an opened/closed state of a valve portion in the lumen of the subject from an image pickup signal obtained by picking up an image of the opened/closed state of the valve portion in the lumen using an endoscope, generating a first superposition image by superposing the first temporal change image and the observation image in a temporally synchronized manner, and measuring a gas release sound released from the lumen of the subject to generate a second temporal change image that is an image showing a temporal change in the gas release sound from a measured value of the gas release sound, and generating a second superposition image by superposing the first temporal change image, the second temporal change image, and the observation image in the temporally synchronized manner.

\* \* \* \* \*